United States Patent
Fox et al.

(10) Patent No.: US 9,833,734 B2
(45) Date of Patent: Dec. 5, 2017

(54) AIR QUALITY INDICATOR

(71) Applicant: 3M INNOVATIVE PROPERTIES COMPANY, St. Paul, MN (US)

(72) Inventors: Andrew R. Fox, Oakdale, MN (US); Liming Xin, Shanghai (CN)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/105,845

(22) PCT Filed: Dec. 3, 2014

(86) PCT No.: PCT/US2014/068266
§ 371 (c)(1),
(2) Date: Jun. 17, 2016

(87) PCT Pub. No.: WO2015/094652
PCT Pub. Date: Jun. 25, 2015

(65) Prior Publication Data
US 2016/0310884 A1    Oct. 27, 2016

Related U.S. Application Data

(60) Provisional application No. 61/917,165, filed on Dec. 17, 2013.

(51) Int. Cl.
*B01D 46/00* (2006.01)
*F24F 3/16* (2006.01)
(Continued)

(52) U.S. Cl.
CPC ....... *B01D 46/0086* (2013.01); *B01D 46/002* (2013.01); *B01D 46/0032* (2013.01);
(Continued)

(58) Field of Classification Search
CPC . B01D 46/0032; B01D 46/0086; F24F 3/166; G01N 15/0625
See application file for complete search history.

(56) References Cited

U.S. PATENT DOCUMENTS 2,753,831 A    7/1956    Davies
2,782,747 A    2/1957    Alderfer
(Continued)

FOREIGN PATENT DOCUMENTS

CN    102380270 A    3/2012
DE    4413148    4/1995
(Continued)

OTHER PUBLICATIONS

Fjeld, Robert A., and Timothy M. Owens. "The effect of particle charge on penetration in an electret filter." IEEE Transactions on Industry Applications 24.4 (1988): 725-731.*
(Continued)

*Primary Examiner* — Lisa Caputo
*Assistant Examiner* — Punam Roy
(74) *Attorney, Agent, or Firm* — Kenneth B. Wood

(57) ABSTRACT

An air quality indicator for indicating high fine particle levels in an environment of interest. The indicator includes a frame maintaining first and second air filter media. The first air filter medium differs from the second air filter medium at least in terms of a change in visual appearance (e.g., color) when subjected to air flow containing fine particles.

15 Claims, 6 Drawing Sheets

(51) Int. Cl.
  *F24F 11/00* (2006.01)
  *G01N 15/06* (2006.01)
  *G01N 1/22* (2006.01)
  *G01N 15/00* (2006.01)

(52) U.S. Cl.
  CPC ............ *F24F 3/1603* (2013.01); *F24F 3/166* (2013.01); *F24F 11/0017* (2013.01); *G01N 1/2205* (2013.01); *G01N 15/0618* (2013.01); *G01N 15/0625* (2013.01); *B01D 2267/40* (2013.01); *F24F 2003/1614* (2013.01); *F24F 2011/0093* (2013.01); *G01N 2015/0046* (2013.01); *Y02B 30/78* (2013.01)

(56) References Cited

U.S. PATENT DOCUMENTS

| | | |
|---|---|---|
| 2,804,839 A | 9/1957 | Hallinan |
| 2,849,005 A | 8/1958 | Tucker |
| 3,027,865 A | 4/1962 | Kautz |
| 3,635,001 A | 1/1972 | Komroff |
| 3,698,871 A | 10/1972 | Brennan |
| 3,916,817 A | 11/1975 | Kemp |
| 4,130,487 A | 12/1978 | Hunter |
| RE30,782 E | 10/1981 | Van Turnhout |
| 4,321,070 A | 3/1982 | Bede |
| 4,336,038 A | 6/1982 | Schultheiss |
| 4,588,537 A | 5/1986 | Klaase |
| 4,955,995 A | 9/1990 | Pontius |
| 5,230,800 A | 7/1993 | Nelson |
| 5,486,410 A | 1/1996 | Groeger |
| 5,496,507 A | 3/1996 | Angadjivand |
| 5,538,690 A | 7/1996 | Greer |
| 5,597,645 A | 1/1997 | Pike |
| 5,662,728 A | 9/1997 | Groeger |
| 5,908,598 A | 6/1999 | Rousseau |
| 5,909,598 A | 6/1999 | Kadohara |
| 5,919,847 A | 7/1999 | Rousseau |
| 5,968,635 A | 10/1999 | Rousseau |
| 5,972,808 A | 10/1999 | Groeger |
| 5,976,208 A | 11/1999 | Rousseau |
| 5,976,467 A | 11/1999 | Dallas |
| 6,057,256 A | 5/2000 | Krueger |
| 6,110,260 A | 8/2000 | Kubokawa |
| 6,187,596 B1 | 2/2001 | Dallas |
| 6,268,495 B1 | 7/2001 | Rousseau |
| 6,268,496 B1 | 7/2001 | Shaw |
| 6,397,458 B1 | 6/2002 | Jones |
| 6,398,847 B1 | 6/2002 | Jones |
| 6,409,806 B1 | 6/2002 | Jones |
| 6,562,112 B2 | 5/2003 | Jones |
| 6,814,909 B1 | 11/2004 | Sakurai |
| 6,858,297 B1 | 2/2005 | Shah |
| 6,979,361 B2 | 12/2005 | Mihayiov |
| 7,695,660 B2 | 4/2010 | Berrigan |
| 7,713,339 B2 | 5/2010 | Johansson |
| 7,758,818 B2 | 7/2010 | Lee |
| 7,858,163 B2 | 12/2010 | Angadjivand |
| 7,947,142 B2 | 5/2011 | Fox |
| 8,162,153 B2 | 4/2012 | Fox |
| 8,225,782 B2 | 7/2012 | Rakow |
| 8,365,723 B2 | 2/2013 | Poirier |
| 8,574,343 B2 | 11/2013 | Bisson |
| 8,790,449 B2 | 7/2014 | Li et al. |
| 2003/0134515 A1 | 7/2003 | David |
| 2003/0182987 A1 | 10/2003 | Bodnar |
| 2004/0011204 A1 | 1/2004 | Both |
| 2007/0272081 A1 | 11/2007 | Johansson |
| 2007/0277592 A1 | 12/2007 | Johansson |
| 2010/0024652 A1 | 2/2010 | Fox |
| 2011/0094514 A1* | 4/2011 | Rakow ................. A62B 18/088 128/206.12 |
| 2011/0185903 A1 | 8/2011 | Fox |
| 2012/0017910 A1 | 1/2012 | Li |
| 2012/0037005 A1 | 2/2012 | Jarrier et al. |
| 2013/0081446 A1 | 4/2013 | Yamasaki |
| 2013/0101477 A1 | 4/2013 | Both |
| 2014/0326134 A1 | 11/2014 | Frankel |

FOREIGN PATENT DOCUMENTS

| | | |
|---|---|---|
| DE | 10 2009 025183 A1 | 12/2010 |
| GB | 2311857 | 10/1997 |
| JP | 3-106286 | 5/1991 |
| JP | 5-137919 A | 6/1993 |
| JP | 5-51426 U | 7/1993 |
| JP | 10-263067 A | 10/1998 |
| JP | 2012-527625 T | 11/2012 |
| KR | 10-2004-0013679 A | 2/2004 |
| KR | 10-2005-0096220 A | 10/2005 |
| KR | 10-2012-0006527 A | 1/2012 |
| WO | WO 88-01050 | 2/1988 |
| WO | WO 2005/100988 | 10/2005 |
| WO | WO 2009/029426 A1 | 3/2009 |
| WO | WO 2010/135417 A2 | 11/2010 |
| WO | WO 2014-149917 | 9/2014 |
| WO | WO 2015-103593 | 7/2015 |

OTHER PUBLICATIONS

International Search Report for PCT International Application No. PCT/US2014/068266, dated Feb. 18, 2015, 2 pages.

Extended European Search Report, EP14872182.2, dated Jul. 17, 2016, 3 pages.

* cited by examiner

AIR QUALITY INDICATOR

BACKGROUND

The present disclosure relates to air quality indicators. More particularly, it relates to easy-to-use indicators of elevated airborne fine particle levels.

Air quality is a rising concern in many parts of the world. One air quality parameter of heightened interest is the levels or amount of fine particles of fine particulate matter. Fine particles or fine particulate matter is commonly designated as particles having a diameter of 2.5 µm or less, and is conventionally referred to by the abbreviation "$PM_{2.5}$". Airborne fine particles can pose significant health risks, especially at elevated levels in relatively confined areas.

Room air purifiers, HVAC filters and other filter-based systems are widely available for removing particles from air, and are highly useful in improving indoor air quality. The filter media utilized with indoor air filtration systems continues to evolve. More recently, filter media viable for indoor has been developed that readily captures fine particles. Electrostatic treatment of filter media is known to significantly improve the ability of a filter media to capture fine particulate matter. With the inclusion of high electrostatic charge processes and materials, filter media (available, for example, from 3M Company of St. Paul, Minn.) can be produced that has both high fine particle efficiency and low airflow resistance.

Notwithstanding the wide availability, many residential and office space environments do not take advantage of fine particulate air quality solutions. It is surmised that the failure to consider or address elevated fine particle levels arises from the simple fact that the human senses cannot readily perceive the presence of airborne fine particles, even at elevated levels, when indoors (although outdoors, fine particles can create haze). If the presence of airborne fine particles is not brought to the attention of the persons living or working in a certain environment, there may be little motivation to make use of fine particle filtration technology. This can be especially troubling in environments where some attempt at large particle air quality control is in place (e.g., filtration media suited for removing only large particles); under these circumstances, persons living or working in the environment may be under the false impression that the overall air quality is acceptable when in fact a potentially unsafe fine particle level exists. Unfortunately, many regions of the world continue to report excessively high fine particulate levels ($PM_{2.5}$). As a point of reference, acceptable fine particle levels have been developed by various governmental entities, typically expressed in terms of total particle weight per unit volume of air over time (e.g., micrograms per cubic meter). For example, in 2012 the US EPA reaffirmed a daily $PM_{2.5}$ air quality standard of 35 µg/m$^3$, and revised downward the annual standard to 12 µg/m$^3$. Recent air quality measurements from major Chinese cities such as Shanghai and Beijing commonly show $PM_{2.5}$ exceeding 100 µg/m$^3$ in fall, winter, and spring, and occasionally exceeding even 500 µg/m$^3$.

While sensor systems for measuring fine particles levels in air are well known and can produce highly accurate data, they are expensive and relatively complex to operate. Scientists and other research professionals require and rely upon the detailed information these sensor systems can provide, thus justifying the costs. In contrast, persons interested in generally understanding fine particle levels on a gross scale have no need for detailed data and will not invest in available sensor equipment. In fact, the data produced by fine particle level sensors may have little meaning to the average person who likely will not otherwise appreciate the implications of a particular value. In short, existing fine particle level sensor technology is not a viable option for persons wishing to determine if an environment of interest has an elevated fine particle level.

In light of generally increasing poor air quality, coupled with a growing awareness of air quality issues, a need exists for simple solutions to indicate both actual air quality and the need for air quality solutions.

SUMMARY

Some aspects in accordance with principles of the present disclosure are directed toward an air quality indicator for indicating high fine particle levels in an environment of interest. The indicator includes a frame maintaining first and second air filter media. The first air filter medium differs from the second air filter medium at least in terms of a change in visual appearance (e.g., color) when subjected to air flow containing fine particles.

In some embodiments, the first air filter medium is a high efficiency filter medium (e.g., highly electrostatically charged) and the second air filter medium is a low efficiency filter medium (e.g., uncharged or lightly charged). Combining the high and low efficiency media into an indicator can provide an indicator with two parallel loading surfaces that initially appear similar (or identical) but which change color at a differential rate when exposed to contaminated air. The indicator can thus provide information about the quality of the air in the location sampled, and can inform a user as to the benefits of adding an electrostatically charged filter media for improving indoor air quality of the environment. Treatments which improve the durability of electrostatic charge toward oily contaminants, such as surface fluorination, may be beneficial in particularly contaminated air.

Active airflow through the indicator can be beneficial in some embodiments to appreciably produce a distinct change in visual appearance of the first air filter medium. Several air-moving devices to which such an indicator may be attached include an air purifier inlet or upstream side of a filter, an HVAC upstream side of a filter, a portable fan, the inlet side of a room or portable air conditioner, and the supply or return duct for an HVAC system. The indicator may also be supplied with its own air-moving device.

It is envisioned that the air quality indicator may commonly cover only a portion, often a small portion, of one of the air-moving surfaces mentioned above. As such, the indicator acts as a partial barrier to air flowing through the overall air-moving surface. The air will want to preferentially flow around, not through, the air quality indicator. Thus, the ability to provide high efficiency but very low pressure drop media for the indicator is optionally important, in some embodiments, to allowing adequate air flow through the indicator to properly indicate the air quality.

Also contemplated is a method for using such an indicator downstream of an HVAC filter. In particular, an indicator may be used downstream of a low efficiency (such as an uncharged media) filter to indicate to the consumer that their filter has not filtered a significant portion of particles in the air, but that an electrostatic filter may deliver improved filtration to their space. This approach may be particularly favorable since the upstream filter, even if low efficiency for fine particles, will likely catch much of the very large particulate matter that might constitute a "false positive" dirty appearance at the indicator.

DETAILED DESCRIPTION

Figure 1:
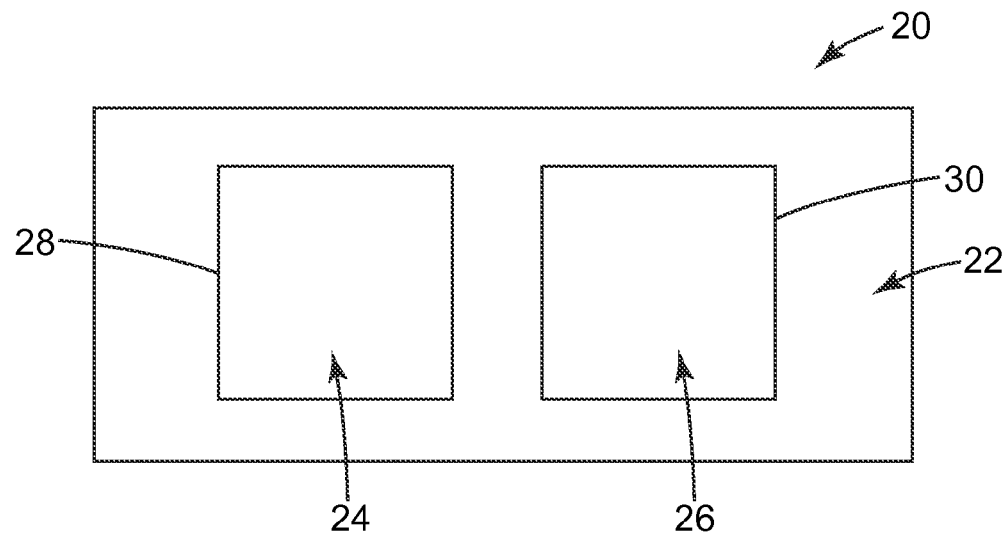
FIG. 1 is a simplified front plan view of an air quality indicator in accordance with principles of the present disclosure.

One embodiment of an air quality indicator 20 in accordance with principles of the present disclosure is show in FIG. 1. The air quality indicator 20 includes a frame 22 maintaining a first air filter medium 24 and a second air filter medium 26. Details on the various components are provided below. In general terms, the frame 22 is relatively small, and retains the filter media 24, 26 in a side-by-side arrangement. The first and second air filter medias 24, 26 can assume a variety of forms, and are both generally capable of allowing air flow through a thickness thereof (i.e., into and out of the page of FIG. 1). The first air filter medium 24 differs from the second air filter medium 26 at least in terms of a rate of change in visual appearance when subjected to fine particle-laden air flow over a relatively short period of time (e.g., on the order of 1-10 days). The change in visual appearance in response to air flow with elevated $PM_{2.5}$ characteristic can be a function of an ability of the air filter media 24, 26 to capture fine particles (e.g., the first air filter medium 24 can readily capture fine particles, whereas the second filter medium 26 captures fine particles to a much lesser extent, if at all). With this construction, the air quality indicator 20 can be located in an environment of interest, for example at a location of prevalent forced air flow. Under circumstances where the air flow contains higher levels of fine particles, over time a visual appearance of the first air filter medium 24 will become distinct from a visual appearance of the second air filter medium 26, thus apprising a user that elevated fine particle levels exist in the environment.

The frame 22 can assume a wide variety of forms, and is generally configured to robustly retain the filter media 24, 26 in the presence of expected air flow rates (e.g., on the order of 02. to 2.0 meters per second). The frame 22 can be made of paperboard, cardboard, corrugated fiber board, plastic, corrugated plastic, or other inexpensive material. Alternatively, the frame 22 can be constructed from a more rigid material, such as metal. The frame 22 forms or defines a pair of windows 28, 30 at which the filter media 24, 26, respectively, are retained. Thus, the filter media 24, 26 are exposed to an external environment of the indicator 20, and more particularly air flow, at the windows 28, 30.

The frame 22 defines an overall footprint of the indicator 20 and is relatively small, for example having a length of not more than 6 inches, alternatively not more than 4 inches, alternatively on the order of 3 inches; a width of not more than 4 inches, alternatively not more than 2 inches, alternatively on the order of 1 inch. Other dimensions (e.g., a length greater than 6 inches and/or a width greater than 4 inches) are also envisioned. Further, while the frame 22 is illustrated as having a rectangular-shaped perimeter, other shapes are also acceptable (e.g., square, circle, irregular, etc.). In other embodiments, a small size or footprint of the frame 22, and thus of the indicator 20, can be characterized by reference to a surface area of the indicator 20, for example a surface area of not more than 24 $in^2$, alternatively not more than 16 $in^2$, alternatively not more than 10 $in^2$, and in some embodiments on the order of 3 $in^2$.

As evidenced by the above descriptions, the frame 22 is desirably simple in shape and construction so as to render the indicator 20 inexpensive and easy to manufacture in some embodiments. In other embodiments, the frame 22 can incorporate, or have assembled thereto, one or more additional components that promote mounting of the indicator 20 at a desired location. For example, and as described in greater detail below, a major face of the frame 22 can include or be coated with a pressure sensitive adhesive or other adhesive composition. In other embodiments, one or more fasteners (e.g., hook, Velcro™, etc.) can be assembled to or provided at one of the major faces of the frame 22.

While the frame 22 has been described as being an integrally formed component, other constructions are envisioned. For example, the frame 22 can consist of two or more sections that are separately formed and subsequently assembled (e.g., when mounting the frame 22 to the air filter media 24, 26). In other embodiments, the first and second air filter media 24, 26 can each be formed with or assembled to a frame or housing, with the two air filter medium frames or housings being subsequently assembled to one another to collectively define the singular frame 22.

Figure 1A:
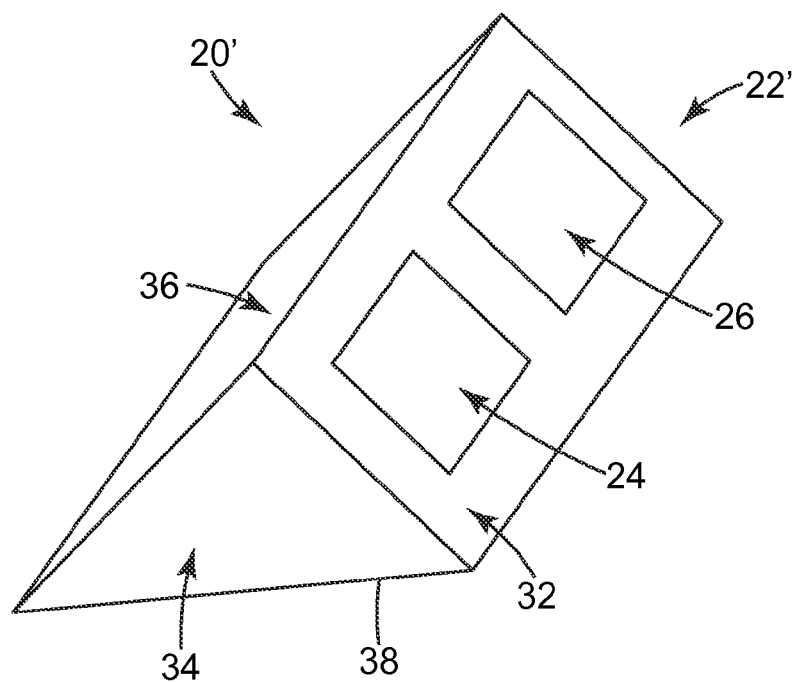
FIG. 1A is a simplified perspective view of another air quality indicator in accordance with principles of the present disclosure and including an alternate frame.

The frame 22 can have the relatively flat shape as shown and described. In other embodiments, indicators of the present disclosure can incorporate frame constructions having a more three dimensional attribute, for example to promote use with certain expected installation locations. FIG. 1A illustrates one optional embodiment indicator 20' including a frame 22' and the air filter media 24, 26. The frame 22' is configured to maintain the air filter media 24, 26 as described elsewhere, and is further configured to direct air flow to the media 24, 26 while maintaining the media 24, 26 at a convenient viewing location relative to an installation site, such as the air inlet of a split air condition.

Figure 1B:
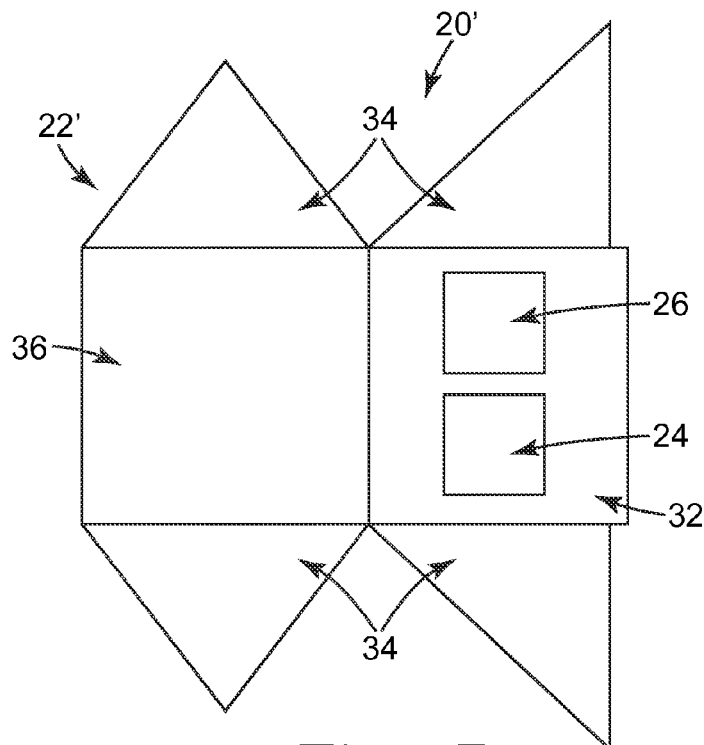
FIG. 1B is a simplified top view of the indicator of FIG. 1A and illustrating the frame in a flat state.

The frame 22' can be configured to be assembled by a user from a flat state (FIG. 1B) to the final state of FIG. 1A. In the final state, the frame 22' defines a front panel 32, opposing side panels 34 (one of which is visible in FIG. 1A), and a top panel 36. The panels 32-36 combine to define an inlet 38 (referenced generally in FIG. 1A) that is assembled over an active air flow surface, with the panels 32-36 directing the air flow to the air filter media 24, 26. Frames of the present disclosure can have a number of other shapes and constructions.

Returning to FIG. 1, the first and second air filter media 24, 26 are in some respects similar, capable of permitting air flow there through (very low pressure drop) and constructed of a generally similar base material as described below. Moreover, prior to exposure to air flow (e.g., prior to use of the indicator 20), the air filter media 24, 26 can have a similar visual appearance, such as a similar color (e.g., white, off-white, etc.). However, the first air filter medium 24 is highly efficient in capturing fine particles, whereas as the second air filter medium 26 exhibits, at best, low efficiency. The captured fine particles coat the surface of the individual fibers of the first air filter medium 24 and cause a darkening of the entire filter medium 24 over time; the same fine particles do not readily collect on the second air filter medium 26 such that the second air filter medium 26 will exhibit minimal, if any, color change (due to presence of fine particles) over time. Optionally, a white pigment (or other color) can be incorporated into each of the media 24, 26 to provide a more distinct "starting" color or appearance (e.g., a white pigment such as titanium dioxide is included or added to the media 24, 26 at acceptable amounts (e.g., 0.1 to 1.0% by mass) to effectuate a more dramatic change in color in the first air filter medium 24, and a more distinct difference in color between the first and second media 24, 26 as the first air filter medium 24 becomes coated with fine particles).

With the above general parameters in mind, the first air filter medium 24 can assume a variety of forms presently known, or in the future developed, constructed or formatted as a high efficiency filter media (i.e., highly efficient in capturing fine particles). The high efficiency attribute can be obtained by imparting an electrostatic charge into or on to material(s) of the first air filter medium 24. The first air filter medium 24 can be a nonwoven fiber web as in known to those of ordinary skill, and when provided with an electrostatic charge, is referred to as an electret nonwoven web in some embodiments. Nonwoven webs useful with the first air filter medium 24 can be formed from a plurality of fibers; as described below, an electrostatic charge can be imparted into the fibers prior to formation of the nonwoven web (e.g., the electret web is formed from electret fibers), or the fibers may not have an electrostatic charge prior to formation of the nonwoven web (with the electrostatic charge being imparted after formation of the web).

Regardless of the stage of manufacture at which the electrostatic charge is imparted, the nonwoven web may have random fiber arrangement and generally isotropic in-plane physical properties (e.g., tensile strength), or if desired may have aligned fiber construction (e.g., one in which the fibers are aligned in the machine direction as described in U.S. Pat. No. 6,858,297 to Shah et al., the teachings of which are incorporated herein by reference) and anisotropic in-plane physical properties.

A variety of polymeric fiber-forming materials may be used as the base material of the first air filter medium 24. The polymer may be essentially any thermoplastic fiber-forming material capable of providing a nonwoven web that will maintain satisfactory electret properties or charge separation. Some preferred polymeric fiber-forming materials for chargeable webs are non-conductive resins having a volume resistivity of $10^{14}$ ohm-centimeters or greater. Polymeric fiber-forming materials for use in chargeable webs can optionally be substantially free from components such as antistatic agents that could significantly increase electrical conductivity or otherwise interfere with the fiber's ability to accept and hold electrostatic charges. Some examples of polymers which may be used in chargeable webs include thermoplastic polymers containing polyolefins such as polyethylene, polypropylene, polybutylene poly(4-methyl-1-pentene), cyclic olefin copolymers, polyesters such as polylactic acid, and combinations of such polymers. In some embodiments the fibers are prepared from polypropylene homopolymer because of its ability to retain electric charge, particularly in moist environments.

Additives may be added to the polymer to enhance the web's ability to attain and maintain satisfactory electret properties, mechanical properties, aging properties, coloring, surface properties or other characteristics of interest. Representative additives include fillers, nucleating agents (e.g., MILLAD™ 3988 dibenzylidene sorbitol, commercially available from Milliken Chemical), electret charging enhancement additives (e.g., tristearyl melamine, and various light stabilizers such as CHIMASSORB™ 119 and CHIMASSORB 944 from Ciba Specialty Chemicals), cure initiators, stiffening agents (e.g., poly(4-methyl-1-pentene)), surface active agents and surface treatments (e.g., fluorine atom treatments to improve filtration performance in oily mist environments as described in U.S. Pat. Nos. 6,398,847, 6,397,458, and 6,409,806 to Jones et al., the entire teachings of each of which are incorporated herein by reference). Other electrostatic charging additives include those described in U.S. Pat. Nos. 6,268,496, 5,976,208, 5,968,635, 5,919,847, and 5,909,598, and U.S. Patent Application Publication No. 2012/0017910. The types and amounts of such additives will be familiar to those skilled in the art. For example, electret charging enhancement additives are generally present in an amount less than about 5 wt. % and more typically less than about 2 wt. %.

In some embodiments, some or all of the fibers comprising the nonwoven webs useful with the first air filter medium 24 are multicomponent fibers having at least a first region and a second region, wherein the first region has a melting temperature lower that the second region. A variety of different types and configurations of multicomponent fibers exists. Suitable multicomponent fibers are described in, for example, U.S. Pat. Nos. 7,695,660, 6,057,256, 5,486,410, 5,662,728, and 5,972,808, the teachings of each of which are incorporated herein by reference in their entireties. The multicomponent fibers can be bicomponent fibers, one of example of which is a sheath/core fiber where the sheath that surrounds the core forms the first region and the core forms the second region of the fiber. Another example of bicomponent fibers useful with the present disclosure are low density bicomponent fibers described, for example, in U.S. Pat. No. 5,597,645, the entire teachings of which are incorporated herein by reference.

Nonwoven webs useful with the first air filter medium 24 can be a high loft spunbond web, such as described, for example, in U.S. Pat. No. 8,162,153 to Fox et al., the entire teachings of which are incorporated herein by reference. In other embodiments, the first air filter medium 24 can be a low loft spunbond web, such as those described in U.S. Pat. No. 7,947,142 to Fox et al., the entire teachings of which are incorporated herein by reference. In yet other embodiments, nonwoven webs useful with the first air filter medium 24 are generated by other techniques and/or have other characteristics, such as the meltblown nonwoven webs disclosed in U.S. Pat. No. 6,858,297 to Shah et al. (mentioned above). Other non-limiting example of useful nonwoven web formats include bi-modal fiber diameter meltblown media such as that described in U.S. Pat. No. 7,858,163, the entire teaching of which are incorporated herein by reference.

Electric charge can be imparted to the nonwoven webs of the first air filter medium 24 in a variety of ways. The fibers can be electrostatically charged before, during and/or after being formed into a nonwoven web. This may be carried out, for example, by contacting the fibers and/or the web with water as disclosed in U.S. Pat. No. 5,496,507 to Angadjivand et al, corona-treating as disclosed in U.S. Pat. No. 4,588,537 to Klasse et al., hydro-charging as disclosed, for example, in U.S. Pat. No. 5,908,598 to Rousseau et al., plasma treating as disclosed in U.S. Pat. No. 6,562,112 to Jones et al. and U.S. Application Publication No. 2003/0134515 to David et al., or combinations thereof, the entire teachings of each of which are incorporated by reference. In some embodiments, the nonwoven web useful as the first air filter medium 24 may be subjected to a charging process that further enhances any charges possessed by the electret fibers and/or may enhance the ability of the fibers to maintain these charges. Thus, in some embodiments electret fibers may be subjected to an initial charging process prior to web formation; and, an additional (final) charging process may be formed on the web in order to reach the desired final charge state of the electret fibers. In other embodiments, the nonwoven webs useful with the first air filter medium 24 may comprises fibers that, although they may comprise e.g., electret charging enhancement additives, did not go through a charging process prior to the fibers being formed into a web. In such particular embodiments, the post-web-formation charging process may include e.g., any or all of corona charging, tribocharging, hydrocharging, corona treatment followed by hydrocharging, and plasma treatment followed by hydrocharging. Such a charging process might be performed e.g., before or after application of a support layer to the nonwoven electret web (thus, in some embodiments, some degree of charging may be imparted to the material of the support layer(s)).

Electret filter webs useful as the first air filter medium 24 can be formed of split fibrillated charged fibers such as described in U.S. Pat. No. RE 30,782 to Van Turnhout et al., the teachings of which are incorporated herein by reference in its entirety. The electret fibers of this reference are formed from a corona charged film that is fibrillated to form the charged fibers. The charged fibers can then be formed into a nonwoven web by common methods such as carding or air laying. The so-provided nonwoven web can optionally be joined (e.g., needle tacked) to a supporting scrim such as disclosed in U.S. Pat. No. 5,230,800, the teachings of which are incorporated herein by reference in its entirety, forming an outer support layer. The first air filter medium 24 thus includes the electret nonwoven web and the support layer. Alternatively, the fibrillated film can be ultrasonically bonded to a supporting scrim such as disclosed in U.S. Patent Application Publication No. 2004/0011204 to Both, the teachings of which are incorporated herein by reference in its entirety.

The second air filter medium 26 can be any low efficiency air filter media (with low or very low pressure drop) currently known or in the future developed. In some embodiments, the second air filter medium 26 is or includes a nonwoven fiber web that is not electrostatically charged, or is treated so as to remove or discharge at least a majority of any electrostatic charge properties. Thus, the second air filter medium 26 can be any of the nonwoven webs (or nonwoven webs assembled to a support structure) described above with respect to first air filter medium 24 in non-electrostatically charged formed (e.g., any polymer fiber nonwoven web constructions described above, except that an electrostatic charge is not imparted on to the fibers before, during or after formation of the nonwoven web). Alternatively or in addition, any of the nonwoven webs described above, including the electret nonwoven webs, can be subjected to electrostatic discharging conditions, for example applying a discharging agent to the nonwoven web or suturing the nonwoven web in a discharging agent. Various discharging agents are known to those of ordinary skill and include, for example, isopropyl alcohol.

Regardless of the exact form, the first and second air filter media 24, 26 are desirably constructed such that prior to use (i.e., prior to being exposed to forced air flow), the first and second air filter media 24, 26 have a similar visual appearance or color. That is to say, prior to use of the indicator 20, to the naked eye the first and second air filter media 24, 26 appear to be the same color (e.g., white or off-white). The first and second air filter media 24, 26 can be substantially similar in size and shape (e.g., within 5% of an identical size and shape), with the size and shape corresponding with the size and shape of the windows 28, 30. The air filter media 24, 26 can be assembled to the frame 22 in a variety of manners appropriate for maintaining fixed mounting in the presence of expected air flows, for example can by an adhesive.

The indicator 20 can be used to evaluate $PM_{2.5}$ levels in an indoor environment of interest in a wide variety of manners, and generally entails associating the indicator 20 with a surface of a source of active air flow in, or leading to, the indoor environment. At the start of the evaluation period, the first and second air filter media 24, 26 have a similar or even identical visual appearance as described above. At the end of the evaluation period (or periodically during the evaluation time frame), for example after one day, one week, or one month, the indicator 20 is visually reviewed. Under circumstances where the air flow at or to the environment of interest has elevated levels of fine particles, the first air filter medium 24 will appear visually distinct or different from the second air filter medium 26 (e.g., the first air filter medium 24 will be darker or appear "dirtier" than the second air filter medium 26). The difference in visual appearance will readily apprise the observer as to the high $PM_{2.5}$ levels. In some embodiments, the frame 22 (or other component of the indicator 20) can include or carry indicia (words, symbols, icons, pictures, etc.) that assist an observer in understanding the meaning of any visually discernible difference in appearance between the two media 24, 26 (e.g., instructions advising that if the first medium 24 is darkened and the second medium 26 is relatively white, a high level of fine particles exists). In some embodiments, the indicator 20 does not provide any $PM_{2.5}$ data or values that might otherwise confuse an un-trained observer (and that might otherwise increase an overall cost of the indicator 20). In other embodiments, the indicator 20 can be configured to display some $PM_{2.5}$ data or information.

Figure 2:
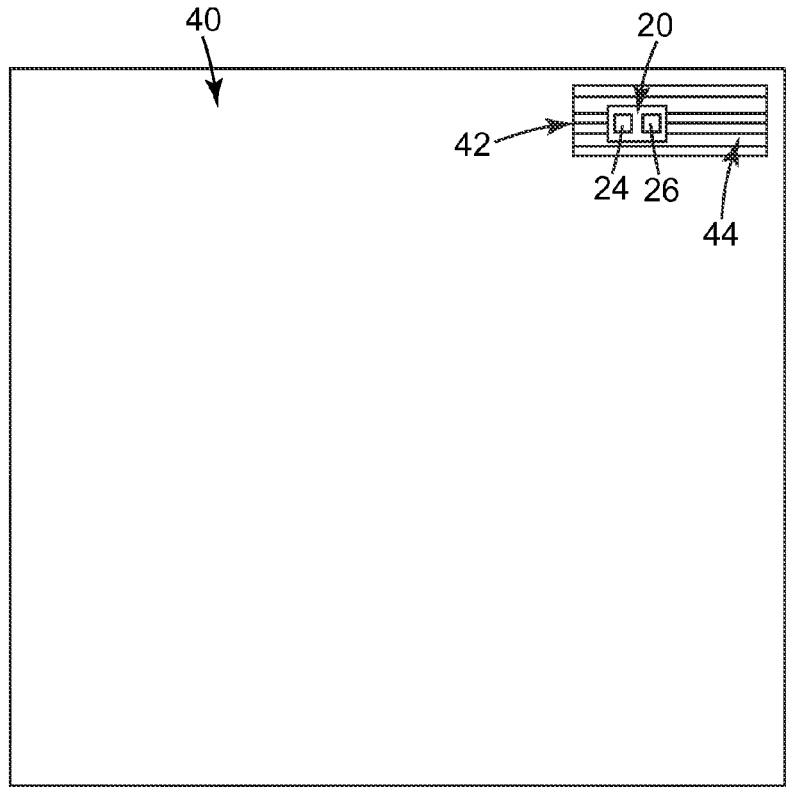
FIG. 2 is a schematic illustration of the indicator of FIG. 1 installed at an environment of interest.

Active air flow through the indicator 20 may be important to generate meaningful results over a relatively short period of time (e.g., 1-10 days). In some embodiments, the source of active air flow in or to the environment of interest is a normal component of the environment's air flow management system, such as an air flow purifier inlet or upstream side of a filter, HVAC filter (upstream or downstream side), a portable fan, a room or portable air conditioner, supply or return duct of an HVAC system, etc. In instances where the selected source of active air flow or air moving device normally operates in an on-demand mode, the indicator 20 may be exposed to periodic air flow, or the user may be instructed or encouraged to operate the air moving device in continuous operation for the duration of the indication period. By way of one non-limiting example, FIG. 2 schematically illustrates an indoor environment of interest 40 in form of a room having a supply air duct 42 partially covered by a conventional grill 44. The indicator 20 is assembled to a face of the grill 44. As shown, the indicator 20 covers only a small portion of the active air flow surface established at or by the grill 44 (or other active air flow surface in the environment of interest). Thus, the indicator 20 acts as a barrier to air flowing through the overall air-moving surface (i.e., the grill 44). However, air flow at the active air flow surface (e.g., the grill 44) occurs through the first and second air filter media 24, 26 due to their low, optionally very low, pressure drop characteristics (i.e., but for the low, optionally very low, pressure drop features, air flow at the active air flow surface would preferentially occur around the indicator 20, thus limiting an overall effectiveness of the indicator 20 in sampling or indicating fine particle levels in the air flow).

The indicator 20 can be assembled to the active air flow surface(s) in the environment of interest in a wide variety of fashions. For example, in some embodiments the indicator 20 includes one or more components that are appropriate for mounting to an active air flow surface expected to be in a room of interest. The attachment component(s) can be assembled to, or provided with, the frame 22. For example, the indicator 20 can carry one or more magnets that can magnetically attach the indicator 20 to one of the metal-based active air flow surfaces commonly found in many indoor spaces (e.g., a metal grate or grill covering an HVAC wall or floor duct). Other attachment components include, but are not limited to, mechanical connectors (e.g., hooks), straps, Velcro, pressure sensitive adhesive, double sided tape, stretch release adhesive strips, etc., to name but a few.

Figure 3:
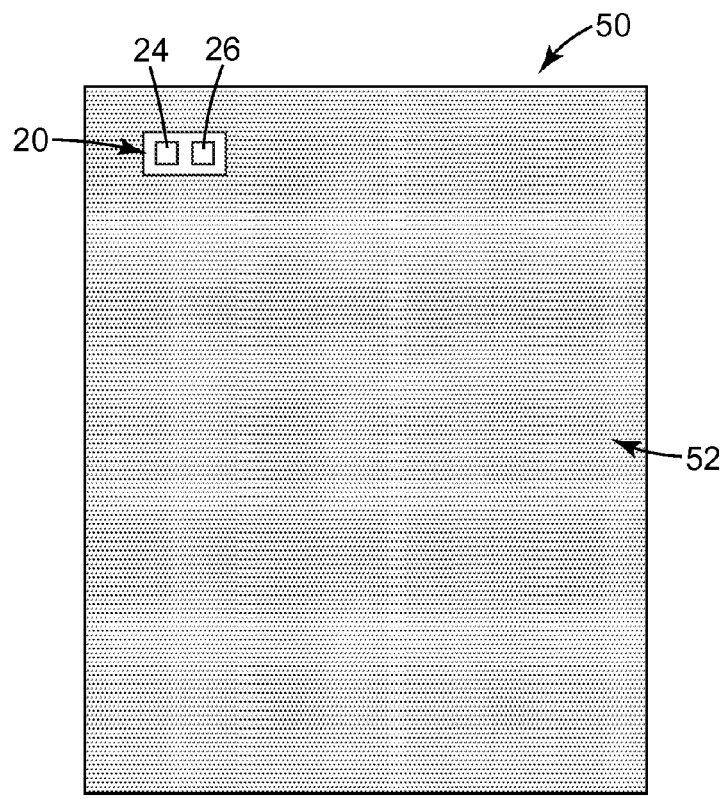
FIG. 3 is a simplified front plan view of an air quality indicator system in accordance with principles of the present disclosure, including the indicator of FIG. 1 and a conventional air filter.

In yet other embodiments, the indicator 20 can be configured in tandem with the active air moving surface. That is to say, air quality indicators in accordance with principles of the present disclosure can include both the indicator as described above in combination with (e.g., pre-assembled to) an active air moving surface normally employed in many indoor environments of interest. For example, the indicators described above can be pre-mounted to an air duct grill or grate, and the indicator grill or grate is used as a temporary replacement for an existing grill or grate in the environment of interest. In yet another example and with reference to FIG. 3, an air quality indicator system 50 in accordance with the present disclosure can include the indicator 20 and an HVAC filter 52. The indicator 20 can assume any of the forms described above. The HVAC filter 52 can be any type of conventional HVAC filter (and of any conventional size), such as any known or in the future developed low efficiency air filter (such as an uncharged filter media). The indicator 20 occupies only a small surface area of the HVAC filter 52, and can be permanently assembled to the intended "downstream" side of the HVAC filter 52. During use, the system 50 is mounted to the HVAC structure associated with the environment of interest in the same manner as would the HVAC filter 52 were the indicator 20 not included. Following a period of operation of the HVAC structure (e.g., days, weeks or even months), the system 50 removed and the indicator 20 visually inspected. Under circumstances where the first air filter medium 24 has become visually distinct from the second air filter medium 26 (e.g., the first air filter medium 24 visually appears much darker or "dirtier" than the second air filter medium 26), the observer will readily understand that the air flow at the environment of interest has an elevated level of fine particles.

Figure 4:
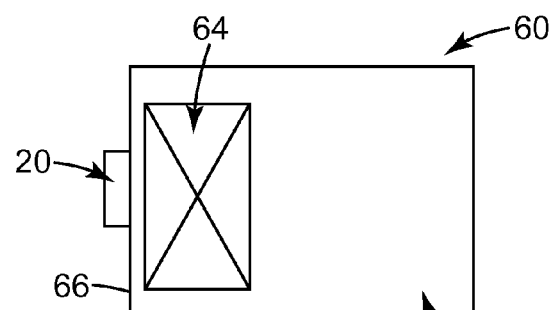
FIG. 4 is a schematic illustration of another indicator system in accordance with principles of the present disclosure and including the indicator of FIG. 1 and an air moving device.

In yet other embodiments, the air quality indicators of the present disclosure can include, or be provided with, an independent source of active air flow. For example, FIG. 4 schematically illustrates another embodiment air quality indicator system 60 in accordance with principles of the present disclosure and includes the indicator 20 assembled to an air moving device 62. The air moving device 62 can assume a wide variety of forms, and in some embodiments is, or includes, a fan 64. The system 60 is highly portable, and the air moving device 62 can be powered in various ways (e.g., the air moving device 62 can carry a power source (e.g., battery), or can be configured for electrical connection to a conventional electrical outlet). Regardless, the indicator 20 is mounted to an active air flow surface 66 of the device 62, and can be used to provide a gross evaluation of fine particles in a room of interest as described above by simply locating the system 60 in the room of interest and operating the air moving device 62 during an evaluation period (e.g., days or weeks or month(s)). The optional incorporation of the dedicated air moving device 62 can allow for the indicator 20 to be sized and shaped so as to substantially or wholly cover the active air flow surface 66.

Figure 5:
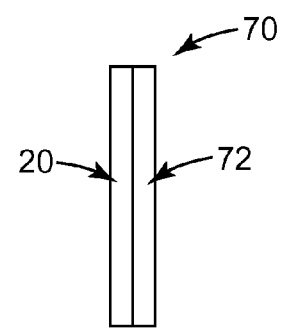
FIG. 5 is a simplified side view of another air quality indicator in accordance with principles of the present disclosure.

Returning to FIG. 1, in some embodiment, the air quality indicators of the present disclosure can provide more meaningful evaluation information when deployed in an active air flow that has already been treated to remove large particles (e.g., air flow that has passed through a low efficiency filter). It will be understood that in some embodiments, both of the air filter media 24, 26 will readily capture large particles; thus, were large particles not substantially removed from the air flow to be evaluated prior to interacting with the air quality indicator, the large particles would accumulate in both of the air filter media 24, 26 possibly resulting in similar discoloration of the media 24, 26 over time (e.g., while the first air filter medium 24 would capture significant amounts of fine particles and the second air filter medium 26 would not capture significant amounts of fine particles, the second air filter medium 26 would still change in visual appearance due to the large particles and may not appear overtly visually distinct from the first air filter medium 24 were the large particles not present). Thus, in some embodiments of the present disclosure, instructions are provided to a user to deploy the indicator 20 at an active air flow location that is downstream of an air flow filtering system. In other embodiments, and with reference to FIG. 5, another air quality indicator system 70 in accordance with principles of the present disclosure includes the air quality indicator 20 and a screen 72 or other large particle filter assembled to the frame 22. The screen 72 is configured to capture significant amounts of large particles (e.g., animal hair, lint, etc.) in an air flow passing through the system 70. During use, a user is instructed to locate the system 70 at the active air flow surface such that the screen 72 is located upstream of the filter media 24, 26 (FIG. 1). During the evaluation period, large particles will collect at the screen 72 and will not overtly impact the filter media 24, 26 such the change in visual appearance, if any, at the first and second filter media 24, 26 is due primarily to fine particles.

EXAMPLES

Example 1

Figure 6:
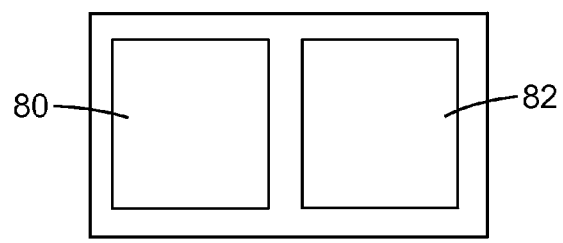
FIG. 6 is a simplified front plan view of a sample indicator prepared in accordance with some examples of the present disclosure.

A series of air quality indicators were prepared using air filter media of a high efficiency filter available from 3M Company under the trade name Filtrete 1900. As shown in FIG. 6, side-by-side media samples with 3.75 inch×3.75 inch open dimension were attached to a cardboard perimeter frame. As labeled in FIG. 6, a first medium 80 was the high efficiency Filtrete 1900 material, whereas a second medium 82 was the Filtrete 1900 material saturated with isopropyl alcohol, then dried, to remove any electrostatic charge prior to installation into the frame. The first medium 80 (i.e., the Filtrete 1900 material) was unaltered.

Air quality evaluations were performed using the air quality indicator samples of Example 1 at three locations. 1) On an outdoor air inlet (thus pulling 100% outdoor air) to a building's HVAC system (located in St. Paul, Minn.) for a period of 14 days. Using accepted fine particle measuring equipment, the average outdoor fine particle level during the evaluation period was found to be 6 $\mu g/m^3$. 2) On an indoor air return at a room in the building of 1) above, for an evaluation period of 14 days. This configuration exposed the indicator to 100% indoor air, which was filtered prior to entering the building through a bank of high efficiency commercial HVAC filters. The average outdoor fine particle level during the evaluation period was estimated to be 6 $\mu g/m^3$. It was noted that the indoor $PM_{2.5}$ level was likely lower than the outdoor $PM_{2.5}$ level as much $PM_{2.5}$ was an outdoor source, and the building HVAC inlet air is filtered at a high level. 3) On the upstream side of a residential HVAC filter located at a residence in St. Paul, Minn., for an evaluation period of 14 days in the summer. The residential HVAC system was run continuously on low speed except for when the system called for on-demand cooling. The average outdoor fine particle level during the evaluation period was estimated to be 5 $\mu g/m^3$. It was noted that the indoor $PM_{2.5}$ level was likely lower than the outdoor $PM_{2.5}$ level as much $PM_{2.5}$ was an outdoor source, and the residential HVAC has minimal outdoor make-up air and included a relatively high level of filtration (via a filter available from 3M Company of St. Paul, Minn. under the trade name 1000 MPR).

Figure 7:
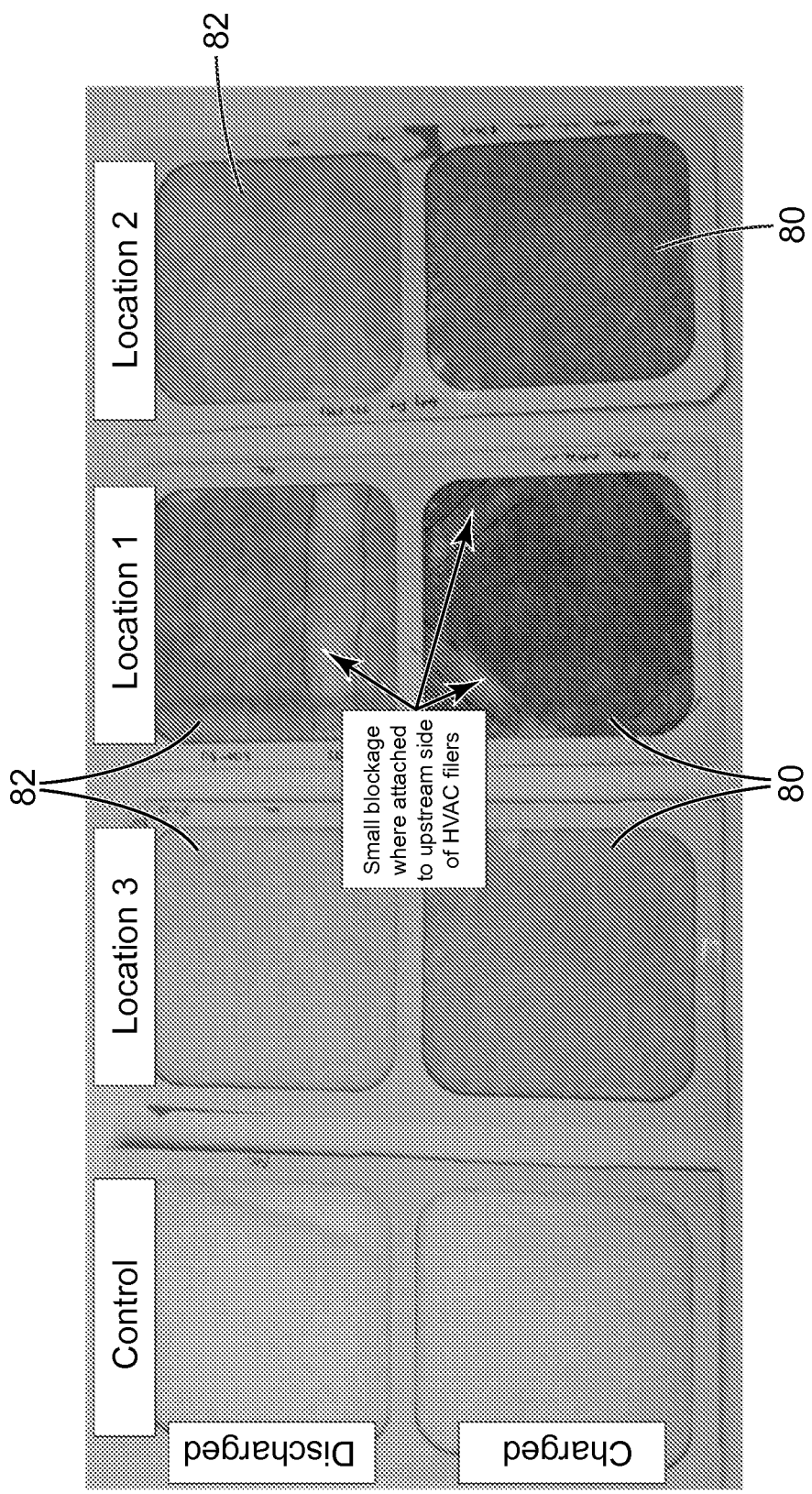
FIG. 7 presents photographs of sample indicators of FIG. 6 following various test evaluations.

FIG. 7 is a photograph of the indicators of Example 1 following an approximately two week evaluation period in their respective environments and with a clean control indicator included for reference. In each of the evaluations, the first medium 80 showed a more substantial color changed than the discharged second medium 82. The indicator exposed to outdoor area (i.e., location 1)) exhibited the greatest color distinction, likely due to exposure to the greatest fine particle concentration.

Example 2

Figure 8:
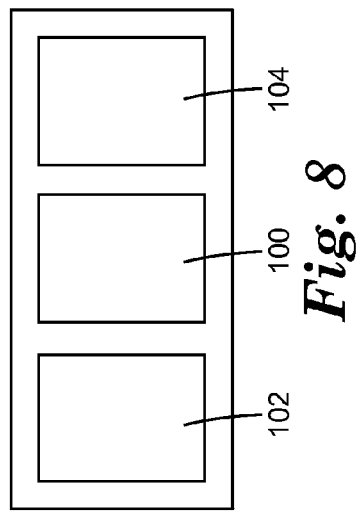
FIG. 8 is a simplified front plan view of another sample indicator prepared in accordance with some examples of the present disclosure.

A series of air quality indicators were prepared using two different media types, as shown in FIG. 8. A first medium 100 was an electrostatically charged filter medium available from 3M Company of St. Paul, Minn. under the trade designation Filtrete 1200. A second medium 102 was the same Filtrete 1200 medium, except discharged by saturation in isopropyl alcohol. A third medium 104 consisted of an uncharged staple fiber web available from Ahlstrom, under the trade designation Model T817. The media 100-104 were approximately 2 inch×3 inch in size, and were attached to a cardboard perimeter frame.

Air quality evaluations were performed using the air quality indicator samples of Example 2 at four locations. 1) On an outdoor air inlet (thus pulling 100% outdoor air) to a building's HVAC system (located in St. Paul, Minn.) for a period of 13 days. Using accepted fine particle measuring equipment, the average outdoor fine particle level during the evaluation period was found to be 6 $\mu g/m^3$. 2) On an indoor air return at a room in the building of 1) above, for an evaluation period of 13 days. This configuration exposed the indicator to 100% indoor air, which was filtered prior to entering the building through a bank of high efficiency commercial HVAC filters. The average outdoor fine particle level during the evaluation period was estimated to be 6 $\mu g/m^3$. It was noted that the indoor $PM_{2.5}$ level was likely lower than the outdoor $PM_{2.5}$ level as much $PM_{2.5}$ was an outdoor source, and the building HVAC inlet air is filtered at a high level. 3) On the upstream side of a residential HVAC filter located at a residence in St. Paul, Minn., for an evaluation period of 13 days in the summer. The residential HVAC system was run continuously on low speed except for when the system called for on-demand cooling. The average outdoor fine particle level during the evaluation period was estimated to be 5 $\mu g/m^3$. It was noted that the indoor $PM_{2.5}$ level was likely lower than the outdoor $PM_{2.5}$ level as much $PM_{2.5}$ was an outdoor source, and the residential HVAC has minimal outdoor make-up air and included a relatively high level of filtration (via a filter available from 3M Company of St. Paul, Minn. under the trade name 1000 MPR). 4) On the upstream side of an air filter provided as part of a residential air purifier. The air filter is available from 3M Company of St. Paul, Minn. under the trade designation FAP02. The air purifier was run on high speed at night only (approximately 11 hours per night) in a closed bedroom for 13 days. The average outdoor fine particle level during the evaluation period was estimated to be 5 $\mu g/m^3$.

Figure 9:
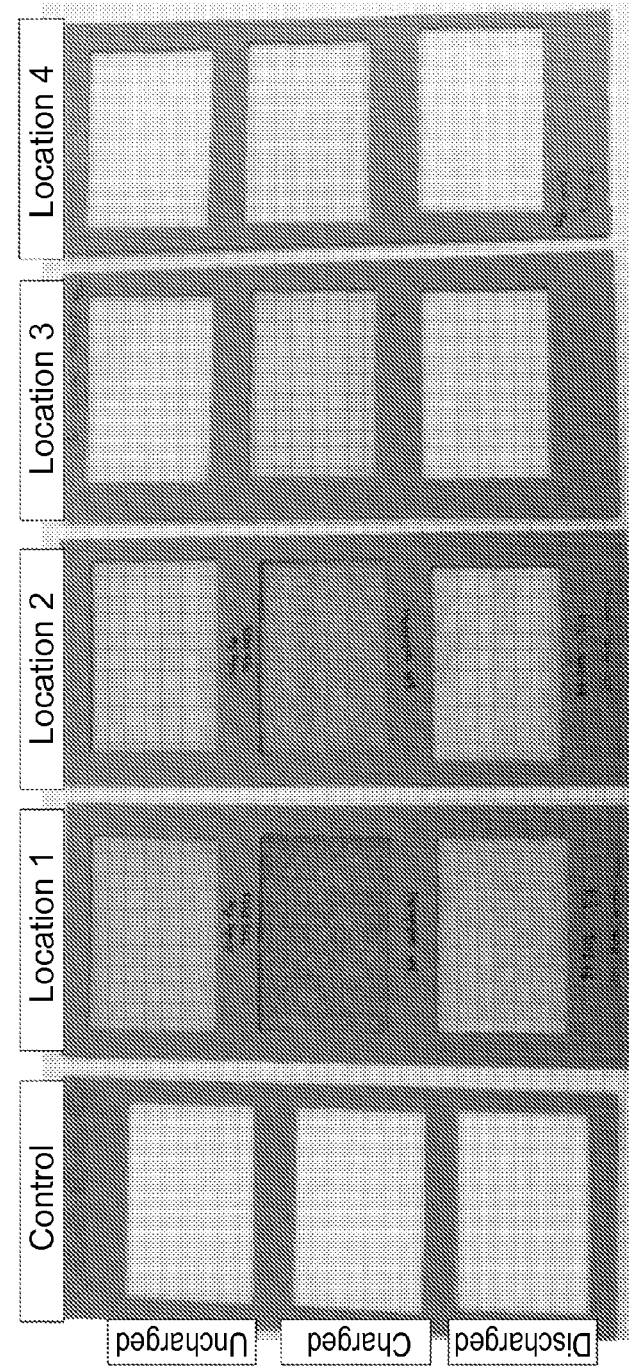
FIG. 9 presents photographs of sample indicators of FIG. 8 following various test evaluations.

FIG. 9 provides photographs of the indicators of Example 2 following an approximately two week evaluation period in their respective environments, along with a clean control indicator for reference. Both of the building locations (i.e., locations 1) and 2)) exhibited the greatest color change, while the residential locations (i.e., locations 3) and 4)) exhibited a lesser total color change. In any of these scenarios, the electrostatically charged medium (i.e., the first medium 100) exhibited a greater color change than either of the uncharged media (i.e., the second and third media 102, 104). The indicator in the residential air purifier scenario (i.e., location 4)) exhibited minimal color change in all three media 100-104.

Example 3

Indicators identical to those of Example 2 were prepared and subjected to air quality evaluations at two locations in Shanghai, China. 1) On an air inlet to a building's split air conditioning system for a period of 7 days. Using accepted fine particle measuring equipment, the average fine particle level during the evaluation period was found to be 34 $\mu g/m^3$. 2) On an HVAC indoor air return in the building of 1) above, for an evaluation period of 7 days.

Figure 10:
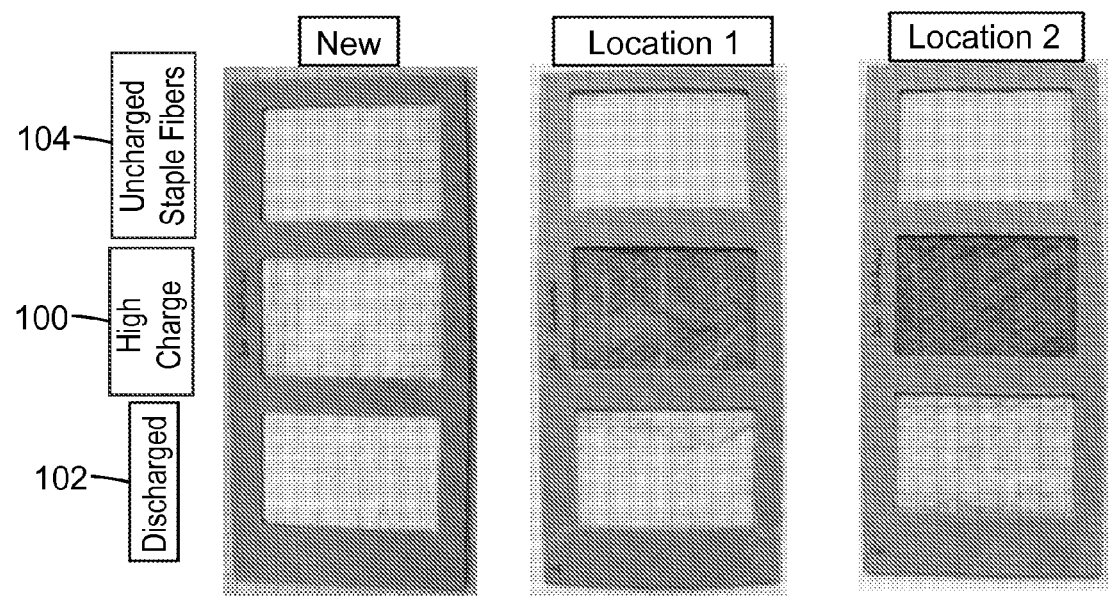
FIG. 10 presents photographs of sample indicators of FIG. 8 following various test evaluations.

FIG. 10 provides photographs of the indicators of Example 3 following an approximately seven day evaluation period, along with a clean control indicator for reference. The seven days of exposure where not seven consecutive days but were staggered for purposes of maintaining a thorough visual record of the color change. Both of the samples exhibited a significant color change, with the HVAC location (i.e., location 2)) showed a slightly greater change in color than the split AC location. In each of the evaluation scenarios, the electrostatically charged web (i.e., the first filter medium 100) exhibited a distinctly greater color change than either of uncharged media (i.e., the second and third media 102, 104), with the difference in color change being readily perceived by the naked eye. The discharged medium (i.e., the second medium 102) exhibited a minor color change, and the uncharged medium (the third medium 104) showed minimal color change at both locations.

The air quality indicators, systems and related methods of use provide a marked improvement over previous designs. The air quality indicators are inexpensive, easy to use, and provide meaningful information regarding fine particle levels to an un-trained user. By combining a high efficiency (e.g., highly electrostatically charged) and low efficiency (e.g., uncharged or lightly charged) media into an indicator can provide an indicator with two parallel loading surfaces that initially appear similar (or identical) but which change color at a differential rate when exposed to contaminated air. The indicator can thus provide information about the quality of the air in the location sampled.

Although the present disclosure has been described with reference to preferred embodiments, those of skill will understand that changes can be made in form and detail with departing from the spirit and scope of the present disclosure. For example, while the air quality indicators have been described as including one high efficiency air filter medium and one low air efficiency filter medium, in other embodiments, the indicator can include two (or more) of the high efficiency air filter media and/or two (or more) of the low efficiency air filter media.

What is claimed is:

1. An air quality indicator for providing an indication of high fine particle levels in air, the indicator comprising:
    a frame defining first and second windows;
    a first air filter medium assembled within the first window;
    a second air filter medium assembled within the second window;
        wherein the first air filter medium is configured to have a rate of change in visual appearance in the presence of high fine particle level air flow that is greater than a rate of change in visual appearance in the presence of high fine particle level air flow of the second air filter medium,
        and wherein the first air filter medium includes an electret nonwoven web and the second air filter medium includes an uncharged nonwoven web.

2. The indicator of claim 1, wherein the air filter media are configured to have a substantially similar appearance prior to exposure to air flow with a high fine particle level.

3. The indicator of claim 1, wherein the air filter media are substantially identical in size and shape.

4. The indicator of claim 1, wherein the frame has a length of no greater than 6 inches and a width no greater than 3 inches.

5. An air quality indicator system for providing an indication of high fine particle levels in air, the system comprising:
    the indicator of claim 1; and
    a large particle filter defining an upstream side and a downstream side;
    wherein the indicator is mounted to the downstream side of the large particle filter.

6. A method of indicating existence of high fine particle levels in air, the method comprising:
    mounting the indicator of claim 1 to an active air flow surface of a source of active air flow;
    operating the source of active air flow to direct air flow through the first and second air filter media; and
    visually comparing an appearance of the first air filter medium with an appearance of the second air filter medium following the step of operating the source of active air flow.

7. The method of claim 6 wherein the indicator is mounted to a face of a grill of an air supply duct.

8. The indicator of claim 1 wherein the frame is comprised of paperboard, cardboard, or plastic.

9. The indicator of claim 1 wherein the first air filter medium and the second air filter medium each comprise a white pigment present at least at 0.1% by mass.

10. The indicator of claim 1 wherein the electret nonwoven web of the first air filter medium comprises a charging enhancement additive.

11. The indicator of claim 1 wherein the first air filter medium is assembled within the first window by an adhesive and wherein the second air filter medium is assembled within the second window by an adhesive.

12. The indicator of claim 1 wherein the indicator comprises at least one magnet.

13. The indicator of claim 1 wherein the indicator is assembled to an air moving device that comprises an electrically powered fan.

14. The indicator of claim 1 wherein the uncharged nonwoven web of the second air filter medium is an uncharged electret web.

15. The indicator of claim 1 wherein the uncharged nonwoven web of the second air filter medium is a discharged electret web.

* * * * *

UNITED STATES PATENT AND TRADEMARK OFFICE
CERTIFICATE OF CORRECTION

PATENT NO. : 9,833,734 B2
APPLICATION NO. : 15/105845
DATED : December 5, 2017
INVENTOR(S) : Andrew Fox Page 1 of 1

It is certified that error appears in the above-identified patent and that said Letters Patent is hereby corrected as shown below:

In the Drawings

<u>Sheet 4 of 6 (Fig. 7)</u>
Line 6 (Approx.), Delete "filers" and insert -- filters --, therefor.

Signed and Sealed this
Thirty-first Day of July, 2018

Andrei Iancu
*Director of the United States Patent and Trademark Office*